United States Patent [19]

Royer

[11] 4,002,531
[45] Jan. 11, 1977

[54] MODIFYING ENZYMES WITH POLYETHYLENE GLYCOL AND PRODUCT PRODUCED THEREBY

[75] Inventor: Garfield P. Royer, Worthington, Ohio

[73] Assignee: Pierce Chemical Company, Rockford, Ill.

[22] Filed: Jan. 22, 1976

[21] Appl. No.: 651,240

[52] U.S. Cl. .......................... 195/68; 195/DIG. 11
[51] Int. Cl.$^2$ ......................................... C07G 7/02
[58] Field of Search ................ 195/68, 63, DIG. 11

[56] References Cited

OTHER PUBLICATIONS

Royer et al., Biochemical and Biophysical Research Communication, vol. 64, No. 2, 1975, pp. 478–484.

*Primary Examiner*—Lionel M. Shapiro

[57] ABSTRACT

A process is disclosed for the preparation of the monoalkyl polyethyleneglycol derivatives of enzymes containing free amino groups. The process involves reductively alkylating the free amino groups of the enzyme with the aldehyde derivative of a monoalkyl polyethyleneglycol.

1 Claim, No Drawings

MODIFYING ENZYMES WITH POLYETHYLENE GLYCOL AND PRODUCT PRODUCED THEREBY

The present invention relates to a process for modifying enzymes with polyethylene glycol.

There has recently been reported certain experimental work which involves attaching polyethyleneglycol to enzymes via reaction of the enzyme with a polyethyleneglycol derivatized triazine. (F. F. Davis, Abstract of the First Chemical Congress of North America, December, 1975). The product is suggested as being useful for enzyme therapy work since it may prevent immunogenicity, may lower susceptibility to proteolysis, and is harmless. For example, the polyethyleneglycol derivatives of the enzymes asparaginase or phenylalanine-$NH_3$ lyase and uricase may be useful for the treatment of leukemia and gout, respectively.

In accordance with the present invention, there is provided a new method for preparing polyethyleneglycol derivatives of enzymes. This method starts with the aldehyde derivative of a monoalkyl polyethyleneglycol (formed by oxidation of the glycol) which is then used to reductively alkylate the enzyme in the presence of sodium borohydride. The method is considered to have the advantages of greater retention of enzymatic activity and greater stability of the glycol derivatized enzymatic product.

The following example illustrates the present invention:

EXAMPLE

Polyethyleneglycol monomethyl ether (1000 M.W.) is oxidized to the corresponding aldehyde with active $MnO_2$. Thereafter the aldehyde is isolated and reacted in aqueous solution (borate buffer pH 8.5, 10 mM benzamidine) with the enzyme trypsin for 10 minutes at 0°–4° C. Royer et al. Biophys. Res. Commun. (1975) 64, 478. The solution is then treated with $NaBH_4$ to yield the monomethyl polyethyleneglycol derivative of the enzyme.

I claim:

1. A process for the preparation of the monoalkyl polyethyleneglycol derivative of an enzyme containing free amino groups comprising reductively alkylating the free amino groups of the enzyme with the aldehyde derivative of a monoalkyl polyethyleneglycol.

* * * * *